United States Patent
Ido et al.

(10) Patent No.: US 9,234,905 B2
(45) Date of Patent: Jan. 12, 2016

(54) METHOD OF CALIBRATING AND CALIBRATION APPARATUS FOR A MOISTURE CONCENTRATION MEASUREMENT APPARATUS

(71) Applicant: Horiba, Ltd., Kyoto (JP)

(72) Inventors: Takuya Ido, Kyoto (JP); Tetsuya Mori, Kyoto (JP)

(73) Assignee: Horiba, Ltd., Kyoto (JP)

( * ) Notice: Subject to any disclaimer, the term of this patent is extended or adjusted under 35 U.S.C. 154(b) by 495 days.

(21) Appl. No.: 13/718,555

(22) Filed: Dec. 18, 2012

(65) Prior Publication Data

US 2013/0166242 A1 Jun. 27, 2013

(30) Foreign Application Priority Data

Dec. 22, 2011 (JP) ................................. 2011-281170

(51) Int. Cl.

| | |
|---|---|
| G01N 35/00 | (2006.01) |
| G01N 21/61 | (2006.01) |
| G06F 19/00 | (2011.01) |
| G01N 21/85 | (2006.01) |
| G01N 21/3504 | (2014.01) |
| G01N 21/27 | (2006.01) |

(52) U.S. Cl.
CPC ........ G01N 35/00693 (2013.01); G01N 21/274 (2013.01); G01N 21/3504 (2013.01); G01N 21/61 (2013.01); G01N 21/8507 (2013.01)

(58) Field of Classification Search
CPC ............ G01N 21/8507; G01N 21/274; G01N 21/3504; G01N 21/61; G01N 35/00693; G01J 3/4338
USPC ................. 702/24, 104, 23; 250/339.13, 343; 356/437
See application file for complete search history.

(56) References Cited

U.S. PATENT DOCUMENTS

| | | | |
|---|---|---|---|
| 6,519,039 B1 * | 2/2003 | Morishita et al. ............. 356/437 |
| 6,748,334 B1 | 6/2004 | Perez | |
| 2008/0179530 A1 | 7/2008 | Liu | |

FOREIGN PATENT DOCUMENTS

JP 2010-096561 A 4/2010

* cited by examiner

*Primary Examiner* — John H Le
(74) *Attorney, Agent, or Firm* — Brooks Kushman P.C.

(57) ABSTRACT

A method of calibrating a gas analysis apparatus that measures the moisture concentration in a gas using a radiating unit includes a moisture concentration measurement value calibrated based on the relationship between the intensity of an absorption spectrum of moisture of a concentration to be measured and the intensity of an absorption spectrum of another component gas that can be measured by the radiating unit, for which the relationship to the intensity of the absorption spectrum of moisture of the measured prescribed concentration is known, and based on the intensity of an absorption spectrum obtained by measuring the other component gas.

9 Claims, 3 Drawing Sheets

METHOD OF CALIBRATING AND CALIBRATION APPARATUS FOR A MOISTURE CONCENTRATION MEASUREMENT APPARATUS

CROSS-REFERENCE TO RELATED APPLICATIONS

This application claims priority under 35 U.S.C. §119 to Japanese Patent Application No. 2011-281170 filed on Dec. 22, 2011. The entire disclosure of Japanese Patent Application No. 2011-281170 is hereby incorporated herein by reference.

BACKGROUND OF THE INVENTION

1. Field of the Invention

The present invention relates to a method of calibrating and a calibration apparatus for a moisture concentration measurement apparatus that measures the moisture concentration in a gas using a light source.

2. Description of the Related Art

Conventionally, the combustion exhaust gas discharged from a boiler that burns coal, heavy oil, and the like contains components such as NOx, SOx, $CO_2$, and CO. Furthermore, gas analysis apparatuses have been developed that analyze the content of these components in a gas. An example of such a gas analysis apparatus that has been developed is one that employs a probe. In a probe type gas analysis apparatus, a measuring beam emitted from a light source is caused to be reflected by a reflector, which is disposed in a tip part of the probe, and the concentration of a prescribed component in the sample gas is analyzed based on information from the measuring beam reflected by the reflector.

In addition, an example of a known probe type gas analysis apparatus is one that comprises a calibration function in addition to a component concentration analysis function.

However, the calibration of a gas analysis apparatus is problematic when measuring the concentration of moisture at 0 degree in Celsius saturation or greater, such as, for example, moisture in an exhaust gas after a combustion process and an exclusion treatment process that uses an aqueous solution. In particular, if calibration is performed using moisture of a high concentration, such as when the dew point is room temperature or greater, then all pipings wherein the gas flows and that include the measurement area must be maintained at the temperature of the dew point or greater. It is difficult to install such calibration equipment in an actual equipment environment, even if it is possible to prepare an environment like that of a laboratory.

To solve such problems, a calibration apparatus for a laser type gas analyzer that can measure moisture concentration has been proposed (refer to Japanese Unexamined Patent Application Publication No. 2010-96561). This apparatus comprises a light emitting unit 250 and a light receiving unit 260; furthermore, a signal processing circuit measures the concentration of a measurement target gas by detecting the second harmonic signal of a modulated signal of a light source unit 204 based on an output signal of a light receiving unit 207. Provided are a piping 301, which hermetically connects both units 250, 260 and maintains a prescribed optical path length of a laser light, a gas washing bottle 500, which supplies air of a prescribed moisture concentration into the piping 301, and an oxygen meter 400, which measures the oxygen concentration of moisture-containing air supplied into the piping 301. The apparatus converts the measured oxygen concentration to moisture concentration, and, using this moisture concentration and the optical path length, calibrates the moisture concentration measurement value produced by the gas analyzer.

In the moisture concentration calibration apparatus recited in Japanese Unexamined Patent Application Publication No. 2010-96561, oxygen concentration before and after bubbling is measured in order to compensate for the concentration of gas generated by the bubbling. However, in this case, the actual calibration procedure is problematic because the calibration apparatus must be transported to the site.

SUMMARY OF THE INVENTION

The present invention was conceived in light of the above-described problem, and its object is to accurately calibrate a moisture concentration measurement value using a comparatively simple procedure.

As the means for solving the problems, a plurality of aspects are explained below. These aspects can be combined arbitrarily as needed.

A method according to one aspect is a method of calibrating a moisture concentration measurement apparatus that measures moisture concentration in a gas using a light source. The method comprises the processes below.

A moisture concentration measurement value is calibrated based on the relationship between an intensity of an absorption spectrum of moisture of a concentration to be measured and an intensity of an absorption spectrum of an other component gas that can be measured by the light source, for which the relationship to an intensity of the absorption spectrum of moisture of the concentration to be measured is known, and based on an intensity of an absorption spectrum obtained by measuring the other component gas. Furthermore, the relationship between the intensities of the absorption spectra is, for example, the ratio of the two or the difference between the two.

A moisture concentration calibration apparatus according to another aspect is a calibration apparatus for a moisture concentration measurement apparatus that measures the moisture concentration in a gas using a light source. The calibration apparatus comprises a storage unit and a calibration unit. The storage unit stores the relationship between an intensity of an absorption spectrum of moisture of the concentration to be measured and an intensity of an absorption spectrum of an other component gas that can be measured by the light source, for which the relationship to the intensity of the absorption spectrum of moisture of the concentration to be measured is known. The calibration unit calibrates a moisture concentration measurement value based on the relationship between the intensity of the absorption spectrum of moisture of the concentration to be measured and the intensity of the absorption spectrum of the other component gas that can be measured by the light source, for which the relationship to the intensity of the absorption spectrum of moisture of the concentration to be measured is known, and based on the intensity of the absorption spectrum obtained by measuring the other component gas.

A storage medium according to another aspect stores a program that causes a computer to perform a step of calibrating a moisture concentration measurement value based on the relationship between an intensity of an absorption spectrum of moisture of a concentration to be measured and an intensity of an absorption spectrum of an other component gas that can be measured by the light source, for which a relationship to the intensity of the absorption spectrum of moisture of the concentration to be measured is known, and based on an intensity of an absorption spectrum obtained by measuring the other component gas.

BRIEF DESCRIPTION OF THE DRAWINGS

Referring now to the attached drawings which form a part of this original disclosure:

DETAILED DESCRIPTION OF THE PREFERRED EMBODIMENT (1) Configuration of Entire Gas Analysis Apparatus A gas analysis apparatus 100 according to one embodiment of the present invention will now be explained, referencing FIG. 1. FIG. 1 is a schematic cross sectional view of the gas analysis apparatus according to one embodiment.

Figure 1:
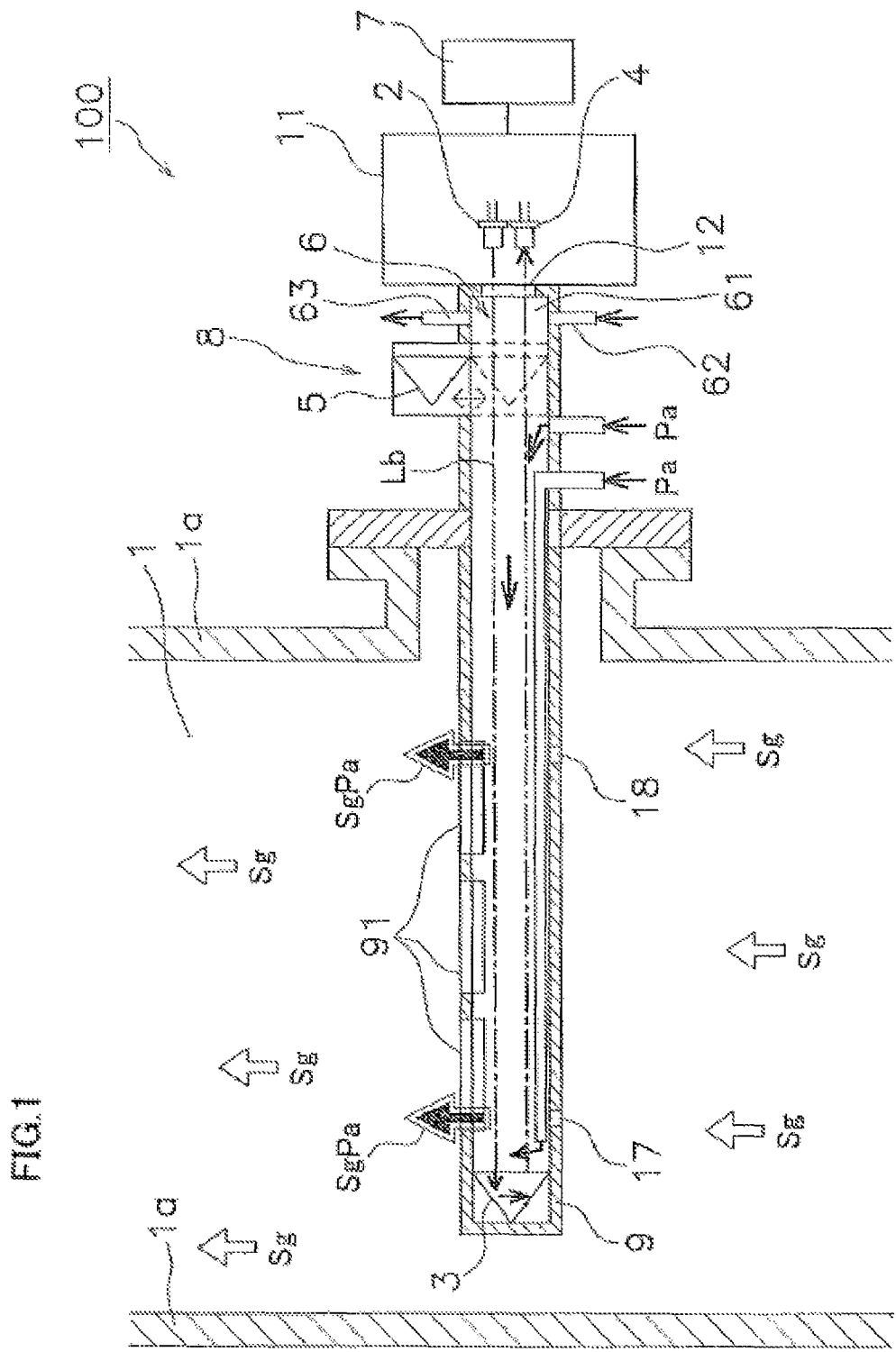
FIG. 1 is a schematic cross sectional view of a gas analysis apparatus according to one embodiment of the present invention.

The gas analysis apparatus is a gas analysis apparatus that analyzes the concentration of a prescribed component in a sample gas that is flowing through a flue 1. The gas analysis apparatus 100 uses laser light and is, for example, a dispersive infrared spectrophotometer or a Fourier transform infrared spectrophotometer.

The gas analysis apparatus 100 comprises one radiating unit 2, a first reflector 3, one light receiving unit 4, a second reflector 5, a known substance housing unit 6, an arithmetic and control unit 7, a switching unit 8, and a probe tube 9. The first reflector 3, the second reflector 5, and the known substance housing unit 6 are housed in the probe tube 9. The radiating unit 2 and the light receiving unit 4 constitute an optical unit and are housed inside a casing 11 of the optical unit. An optical window 12 is disposed at the location at which the casing 11 and the probe tube 9 are connected. The optical window 12 is a plate shaped member that is formed of a raw material wherethrough a measuring beam Lb transmits.

The probe tube 9 is a cylindrical member that is provided with introduction holes 91 that introduce a sample gas Sg into the interior by diffusion. An arbitrary metal material may be selected as the material of the probe tube 9 in accordance with the environment in which the gas analysis apparatus 100 is used. The introduction holes 91 are formed as discontinuous slits in a side surface of the probe tube 9. The first reflector 3 is provided at a tip part inside the probe tube 9. Moreover, the second reflector 5 and the known substance housing unit 6 are provided at a base end part inside the probe tube 9.

The radiating unit 2 is disposed on an outer side of a wall 1a that constitutes the tubular flue 1, and radiates the measuring beam Lb into the sample gas Sg that flows inside the flue 1. The radiating unit 2 typically is a light source apparatus, such as an infrared laser oscillation apparatus, that emits light of a high rectilinearity and of a prescribed wavelength band.

The first reflector 3 reflects the measuring beam Lb emitted from the radiating unit 2 and that passes through the flue 1 toward the light receiving unit 4. Namely, the first reflector 3 is a device for changing the direction of the light (i.e., the optical axis) emitted from the radiating unit 2 such that the light travels toward the light receiving unit 4, and is, for example, a corner cube.

The light receiving unit 4 is disposed in the vicinity of the radiating unit 2 and on the outer side of the wall 1a, and receives the measuring beam Lb reflected by the first reflector 3. The light receiving unit 4 is a light receiving apparatus that receives the measuring beam Lb at a light receiving surface. The light receiving unit 4 is typically a photoelectric conversion device such as a photodiode. The light receiving unit 4 is electrically connected to the arithmetic and control unit 7 and transmits information (e.g., luminous energy) related to the received measuring beam Lb to the arithmetic and control unit 7 as an electrical signal.

The second reflector 5 is disposed on the outer side of the wall 1a and reflects the measuring beam Lb toward the light receiving unit 4. Namely, the second reflector 5 is a devices for changing the direction of the light (i.e., the optical axis) emitted from the radiating unit 2 such that the light travels toward the light receiving unit 4, and is, for example, a corner cube.

In addition, as shown in FIG. 1, holes 17, 18 are formed in the probe tube 9 on both end sides of the surface opposing the introduction holes 91 (i.e., on the upstream side of the flow of the sample gas Sg). By flowing in the sample gas Sg via these holes 17, 18, purge air Pa can be prevented from flowing into the center part of the probe tube 9 and can thereby be caused to mix with the sample gas Sg and discharged from the introduction holes 91 (i.e., as SgPa). The measurement site in the measurement environment lies between the holes 17, 18 discussed above, and the length thereof is defined as the optical path length.

The known substance housing unit 6 is provided in a space area along the optical path between the radiating unit 2 and second reflector 5 and between the second reflector 5 and light receiving unit 4, and houses a known substance that either does not attenuate or attenuates by a prescribed amount the measuring beam Lb radiated from the radiating unit 2. Here, the "known substance" is preferably a substance that, when irradiated with the measuring beam Lb, the luminous energy that transmits therethrough is known in advance, and includes, for example, a zero gas or a span gas as well as an optically transmissive plate or an optical element that is either completely transparent to the measuring beam Lb or that limits the amount of the measuring beam Lb that transmits therethrough to a prescribed amount. In this embodiment, the known substance housing unit 6 is filled with a gas (e.g., a zero gas or a span gas) of a known concentration that is used for correcting or calibrating the gas analysis apparatus 100. The known substance housing unit 6 can comprise, for example, a cell 61 that is optically transmissive, a gas introduction pipe 62 that supplies a known gas into the cell 61, and a gas discharge pipe 63 that discharges the known gas from the interior of the cell 61. Furthermore, the configuration of the known substance housing unit 6 is not limited to the configuration mentioned above; for example, a configuration may be adopted wherein the cell 61 that is optically transmissive is not provided and a known gas is introduced and fills the space area between the optical window 12 and the second reflector 5 in the state wherein the second reflector 5 is disposed along the optical path.

The switching unit 8 is disposed on the outer side of the wall 1a; when component concentration analysis is being performed, the switching unit 8 removes the second reflector 5 from the optical path; furthermore, when correction or calibration is being performed, the switching unit 8 disposes the second reflector 5 along the optical path.

(2) Configuration of Arithmetic and Control Unit

Figure 2:
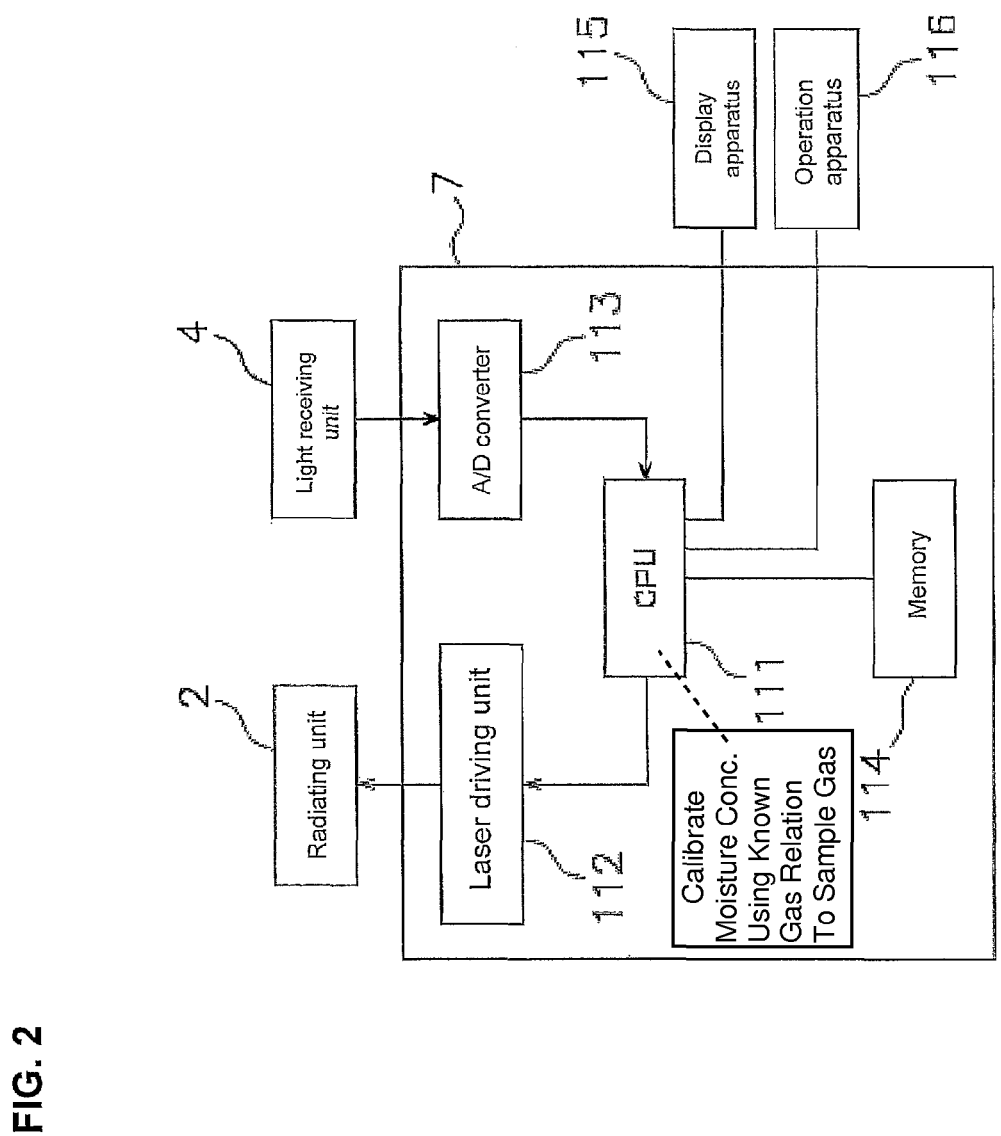
FIG. 2 is a block diagram that shows the configuration of an arithmetic and control unit.

Next, the arithmetic and control unit 7 will be explained, referencing FIG. 2. FIG. 2 is a block diagram that shows the configuration of the arithmetic and control unit.

The arithmetic and control unit 7 comprises control functions that control the operation of the radiating unit 2, the light receiving unit 4, and the switching unit 8. Thereby, the radiating unit 2 emits the measuring beam Lb, the measuring beam Lb is caused to be reflected by the first reflector 3, and the reflected light impinges the light receiving unit 4. Furthermore, the arithmetic and control unit 7 has an arithmetic function that analyzes the component concentration of the sample gas Sg inside the probe tube 9 based on the reflected light detected by the light receiving unit 4. Furthermore, the arithmetic and control unit 7 has a calibration function (discussed below) that uses a known gas to correct or calibrate the gas analysis apparatus 100 by causing the measuring beam Lb emitted from the radiating unit 2 to be reflected by the second reflector 5.

The arithmetic and control unit 7 typically comprises: an information processing apparatus, such as a central processing unit (CPU); a storage apparatus, such as memory; an interface apparatus, which accepts a user operation; and a display apparatus, which displays an analysis result; furthermore, the arithmetic and control unit 7 performs a control process, an arithmetic process, and a calibration process based on a user operation and a program that is stored in the storage apparatus.

In further detail, the arithmetic and control unit 7 comprises a CPU 111, a laser drive unit 112, an A/D converter 113, and memory 114. The CPU 111 is capable of implementing the various functions discussed above. The laser drive unit 112 drives the radiating unit 2 based on a drive instruction from the CPU 111. The A/D 113 converter performs A/D conversion of the detection signal from the light receiving unit 4 and transmits such to the CPU 111. The memory 114 stores the program and various data. Furthermore, a display apparatus 115 and an operation apparatus 116 are connected to the CPU 111. The display apparatus 115 is, for example, a liquid crystal display. The operation apparatus 116 is, for example, a keyboard, a mouse, or a touch panel.

(3) Method of Calibrating the Moisture Concentration Measurement Value

Figure 3:
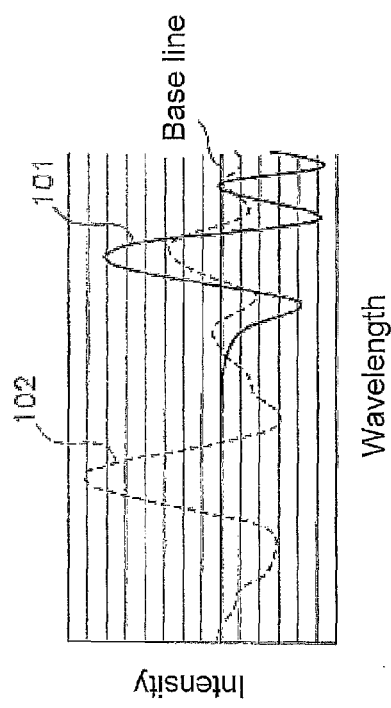
FIG. 3 is a graph that shows the relationship between an absorption spectrum for a moisture concentration of 1.1% and an absorption spectrum for an ammonia concentration of 120 ppm.

Next, a method of calibrating the moisture concentration measurement value will be explained, referencing FIG. 3. FIG. 3 is a graph that shows the relationship between an absorption spectrum for a moisture concentration of 1.1% and an absorption spectrum for an ammonia concentration of 120 ppm. An absorption spectrum for moisture 101 is indicated by a solid line, and an absorption spectrum for an ammonia 102 is indicated by a broken line.

A general example of acquiring the abovementioned absorption spectrums will now be explained. If, for example, the moisture concentration and the ammonia concentration are to be measured using a wavelength variable type laser, then the absorption spectrum is acquired as follows. The wavelength of the laser light is modulated by controlling the current impressed upon the laser (wavelength modulation). The absorption spectrum is then acquired by detecting a harmonic component of the laser light that has a modulation frequency of an integral multiple of the frequency at which the wavelength of the laser light varied by the wavelength modulation. Specifically, the radiating unit 2 emits the wavelength-modulated measuring light Lb with a prescribed modulation frequency toward the sample gas Sg. Then, the light receiving unit 4 receives the measuring light Lb passed through the sample gas Sg, that includes moisture and ammonia, in the flue 1. A signal from the light receiving unit 4 is then subject to A/D conversion. The CPU 111 then extracts a second harmonic component of the measuring light Lb that is received with the light receiving unit 4 from the signal that is A/D converted. Here, the second harmonic component is a signal with a frequency twice as large as that of the modulation frequency. The second harmonic component of the measuring light Lb that is acquired as above is used as the absorption spectrum in the present embodiment.

As is obvious from FIG. 3, within the same wavelength region, the signal strength of the water and the signal strength of the ammonia are identical. Thus, the information that the signal output of the gas that contains water of a prescribed concentration and the signal output of the gas that contains a specific component of a prescribed concentration are substantially the same in the measurement environment is acquired in advance. This means that the relationship between the absorption coefficient $\epsilon$ of water and the absorption coefficient $\epsilon$ of ammonia used in the measurement is ascertained. The CPU 111 acquires, and stores in the memory 114, the abovementioned relationship information (i.e., the relationship between an absorption spectrum intensity of moisture of a concentration to be measured and an absorption spectrum intensity of an other component gas of a first concentration measurable by the radiating unit 2, for which the ratio to the absorption spectrum intensity of the moisture of the concentration to be measured is known).

The method of calibrating the moisture concentration measurement value is explained below. Furthermore, the operation of controlling the various apparatuses below is performed mainly by the CPU 111 of the arithmetic and control unit 7. First, the second reflector 5 is lowered and a calibrating gas that contains ammonia is introduced into the known substance housing unit 6. This step is followed by the step in which the radiating unit 2 emits the measuring beam Lb, and the light reflected by the second reflector 5 is input by the light receiving unit 4. As a result, the CPU 111 acquires the signal output during the measurement of the calibrating gas. Based on this acquired signal output, the CPU 111 calculates a coefficient, which is used in the calibration of the moisture concentration measurement value.

The details of the abovementioned calibration are explained below. The absorption intensity (i.e., the absorbance) of the gas is obtained based on the Lambert-Beer law ($\alpha = \epsilon c L$). Therein, $\alpha$ is the absorbance, $\epsilon$ is the absorption coefficient, c is the concentration, and L is the optical path length. Here, the absorption coefficient $\epsilon$ differs for each absorption line even for the same gas type and also varies with the calibration environment (e.g., the temperature and the pressure).

If it were desired, for example, to make equal to 1 the signal output of the gas that contains moisture of a concentration of 1% in the measurement environment, then relationship information wherein the signal output of 1% moisture and the signal output of a gas of a component A with a concentration of 1,000 ppm are the same would be obtained beforehand. Furthermore, if the condition under which the gas of the component A (ammonia in the present embodiment) was measured were an optical path length L=10 cm with respect to the known substance housing unit 6 and a concentration c=100 ppm, then the signal output would be 0.9. In addition, the optical path length L=100 cm with respect to the measurement area in the measurement environment.

In that case, the equation below holds.

$$\text{Optical absorption } \alpha = \frac{0.9}{10\ \text{cm} \times 100\ \text{ppm}} = \frac{x}{100\ \text{cm} \times 1000\ \text{ppm}} \quad \text{Equation 1}$$

Based on the above equation, an output signal x of the component A at 1,000 ppm (=the output signal of 1% water) is derived. The moisture concentration measurement value is calibrated using this x value. For example, if it is desired that the signal output in this measurement environment be equal to 1, then the value prior to the calibration of the measured measurement value of the moisture concentration is multiplied by 1/x.

Furthermore, using ammonia for the above-described method for calibrating the moisture concentration measurement value has the following advantages. First, the wavelength sweep range in performing the wavelength modulation described above can be narrowed because, within the same wavelength region, the signal strengths of water and ammonia are identical. Thus, the time to measure and collect data for the calibration can be shortened. As a result, the calibration time can be shortened. In addition, because the time to measure and collect data is shortened, the rise in the temperature owing to the injection current to the laser can be reduced. Thus, the variation of the wavelength of the laser light due to the increase of the temperature can be reduced. As a result, the measurement accuracy can also be improved.

Figure 4:
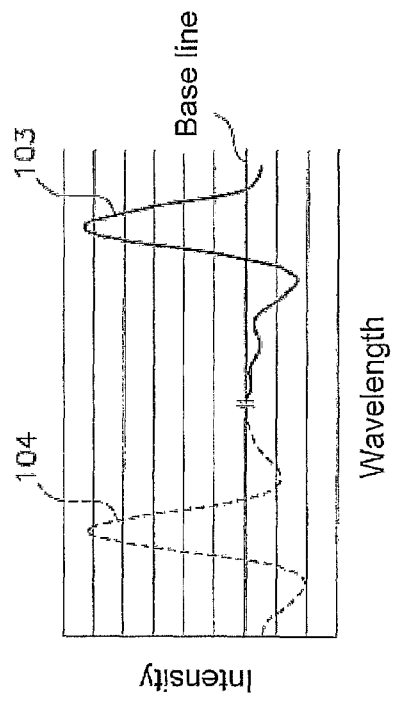
FIG. 4 is a graph that shows the relationship between an absorption spectrum for a moisture concentration of 4% and an absorption spectrum for a hydrogen chloride concentration of 40 ppm.

FIG. 4 is a graph that shows the relationship between a water absorption spectrum for a moisture concentration of 4% and a hydrogen chloride absorption spectrum for a concentration of 40 ppm. A water absorption spectrum 103 is indicated by a solid line, and a hydrogen chloride absorption spectrum is indicated by a broken line 104. As is obvious from FIG. 4, even in different wavelength regions, the signal strengths of the water and the hydrogen chloride are identical. Even though both of the wavelength regions differ, as long as they are within a wavelength region in which the laser is capable of oscillating, the absorption lines that are in the different wavelength regions can be used for the calibration. This is because the sweeping wavelength region can be changed with a high reproducibility by changing the temperature of the laser and injection current to the laser.

(4) Operation and Effects of the Embodiments

The abovementioned embodiments can be described as below.

(A) The abovementioned calibrating method is a method of calibrating the gas analysis apparatus 100 (i.e., one example of a moisture concentration measurement apparatus) that measures the moisture concentration in a gas using the radiating unit 2 (i.e., one example of a light source). This method comprises the processes below.

The moisture concentration measurement value is calibrated based on the relationship between the intensity of the absorption spectrum of moisture of a concentration to be measured and the intensity of the absorption spectrum of the other component gas measurable by the radiating unit 2, for which the relationship to the intensity of the absorption spectrum of moisture of the concentration to be measured is known, and based on the intensity of the absorption spectrum obtained by measuring the other component gas.

In this method, because the moisture concentration measurement value is calibrated based on the relationship between the intensity of the absorption spectrum of moisture of the concentration to be measured and the intensity of the absorption spectrum of the other component gas, for which the relationship to the intensity of that absorption spectrum of moisture is known, and based on the intensity of the absorption spectrum obtained by measuring the other component gas, the moisture concentration measurement value can be calibrated accurately with a comparatively simple procedure. As a result, the cost of calibrating the moisture concentration measurement value is reduced, and furthermore the operation of calibrating the moisture concentration measurement value is performed more easily.

(B) The intensity of the absorption spectrum of moisture of the measured prescribed concentration and the intensity of the absorption spectrum of the other component gas are substantially the same. However, they do not necessarily have to be the same. This is because if the ratio of both is known, then the Lambert-Beer law can be used.

(C) The arithmetic and control unit 7 (i.e., one example of a calibration apparatus) is used in a moisture concentration measurement apparatus 100 (i.e., one example of a moisture concentration measurement apparatus), which uses a light source to measure the moisture concentration in a gas. The arithmetic and control unit 7 comprises the memory 114 (i.e., one example of a storage unit), and the CPU 111 (i.e., one example of a calibration unit). The memory 114 stores the relationship between the intensity of the absorption spectrum of moisture of the concentration to be measured and the intensity of the absorption spectrum of the other component gas that can be measured by the radiating unit 2, for which the relationship to the intensity of the absorption spectrum of moisture of the concentration to be measured is known. The CPU 111 calibrates the moisture concentration measurement value based on the relationship between the intensity of the absorption spectrum of moisture of the concentration to be measured and the intensity of the absorption spectrum of the other component gas that can be measured by the radiating unit 2, for which the relationship to the intensity of the absorption spectrum of moisture of the measured prescribed concentration is known, and based on the intensity of the absorption spectrum obtained by measuring the other component gas.

(D) The CPU 111 comprises a measurement function (i.e., one example of a measurement unit) and the arithmetic function (i.e., one example of a arithmetic function). The measurement function measures, using the radiating unit 2 in the calibration environment, the intensity of the absorption spectrum of the other component gas. The arithmetic function uses the intensity of the absorption spectrum of the other component gas measured in the calibration environment using the radiating unit 2 to calculate, based on the Lambert-Beer law, the intensity of the absorption spectrum of the other component gas at an optical path length of the measurement area in the measurement environment (i.e., one example of a measurement environment) using the radiating unit 2, and calibrates the moisture concentration measurement value based on the intensity of that absorption spectrum.

(5) Other Embodiments

The above explained one embodiment, but the present invention is not limited to that embodiment, and it is understood that variations and modifications may be effected without departing from the spirit and scope of the invention. In particular, the plurality of embodiments and modified examples recited in the present specification can be arbitrarily combined as needed. (a) The structure of the gas analysis apparatus is not limited to the embodiments. (b) Instead of separately introducing the gas of a known concentration, a gas cell, wherein a gas of a known concentration is encapsulated, may be provided inside the gas analysis apparatus. (c) A gas in the atmosphere (e.g., oxygen or carbon dioxide) whose concentration changes very little may be used as the gas of a known concentration.

What is claimed is:

1. A method of calibrating a moisture concentration measurement apparatus that measures the moisture concentration in a sample gas using a light source, the method comprising:
   (a) deriving an intensity of an absorption spectrum of a known substance which is not moisture at a first concentration;
   (b) deriving an intensity of an absorption spectrum of moisture at a second concentration, the intensity of the absorption spectrum of moisture at the second concentration being derived based on the intensity of the absorption spectrum for the known substance at the first concentration derived in (a) and an intensity ratio of the absorption spectra for the known substance and for the moisture known in advance, and
   (c) calibrating a moisture concentration measurement value based on the intensity of the absorption spectrum of the moisture at the second concentration derived in (b).

2. The method of calibrating the moisture concentration measurement apparatus according to claim 1, wherein the intensity ratio is substantially unity.

3. The method of calibrating the moisture concentration measurement apparatus according to claim 1, wherein (a) comprises:
   measuring the intensity of the absorption spectrum of the known substance in a calibration environment using the light source; and
   calculating, based on a Lambert-Beer law, using the intensity of the absorption spectrum of the known substance measured in the calibration environment using the light source, the intensity of the absorption spectrum of the known substance in a measurement environment.

4. The method of calibrating the moisture concentration measurement apparatus according to claim 1, wherein, in (c), the moisture concentration measurement value is calibrated in a manner in which an intensity to be measured for moisture is divided by the intensity for the moisture derived in (b).

5. A calibration apparatus for a moisture concentration measurement apparatus that measures the moisture concentration in a gas using a light source, comprising:
   a storage unit configured to store an intensity ratio of an absorption spectra for a known substance which is not moisture and for the moisture, the intensity ratio being known in advance;
   a control unit configured to derive an intensity of an absorption spectrum of the known substance at a first concentration and an intensity of an absorption spectrum of the moisture at a second concentration, the control unit deriving the intensity of the absorption spectrum of the moisture at the second concentration based on the derived intensity for the known substance at the first concentration and the intensity ratio stored in the storage unit; and
   wherein the control unit is configured to calibrate a moisture concentration measurement value based on the intensity for the moisture at the second concentration.

6. The calibration apparatus for the moisture concentration measurement apparatus according to claim 5, wherein the intensity ratio is substantially unity.

7. The calibration apparatus for the moisture concentration measurement apparatus according to claim 5, wherein the control unit is configured to:
   a measurement unit configured to measure, in a calibration environment and using the light source, the intensity of the absorption spectrum of the known substance; and
   to calculate, based on a Lambert-Beer law, using the intensity of the absorption spectrum of the known substance measured in the calibration environment using the light source, the intensity of the absorption spectrum of the known substance in the measurement environment using the light source, and and derive the intensity of the absorption spectrum of the moisture at the second concentration based on the intensity for the known substance at the first concentration and the intensity ratio stored in the storage unit.

8. The calibration apparatus for the moisture concentration measurement apparatus according to claim 5, wherein the moisture concentration measurement value is calibrated in a manner in which an intensity to be measured for moisture is divided by the intensity of the absorption spectrum of the moisture at the second concentration.

9. A non-transitory storage medium storing a program that causes a computer to perform:
   (a) deriving an intensity of an absorption spectrum of a known substance which is not moisture at a first concentration;
   (b) deriving an intensity of an absorption spectrum of moisture at a second concentration,
   the intensity of the absorption spectrum of moisture at the second concentration being derived based on the intensity of the absorption spectrum for the known substance at the first concentration derived in (a) and an intensity ratio of the absorption spectra for the known substance and for the moisture known in advance, and
   (c) calibrating a moisture concentration measurement value based on the intensity of the absorption spectrum of moisture at the second concentration derived in (b).

* * * * *

UNITED STATES PATENT AND TRADEMARK OFFICE
CERTIFICATE OF CORRECTION

| | |
|---|---|
| PATENT NO. | : 9,234,905 B2 |
| APPLICATION NO. | : 13/718555 |
| DATED | : January 12, 2016 |
| INVENTOR(S) | : Takuya Ido et al. |

Page 1 of 1

It is certified that error appears in the above-identified patent and that said Letters Patent is hereby corrected as shown below:

Claims

Column 10, Lines 18-19, Claim 7:

After "control unit is configured to"
Delete "a measurement unit configured to"

Column 10, Line 26, Claim 7:

After "in the measurement environment"
Delete "using the light source and"

Signed and Sealed this
Twelfth Day of April, 2016

Michelle K. Lee
*Director of the United States Patent and Trademark Office*